United States Patent [19]

Kush et al.

[11] Patent Number: 4,858,478
[45] Date of Patent: Aug. 22, 1989

[54] BELLOWS TYPE HAND-OPERATED AIR SAMPLING PUMP

[75] Inventors: Robert S. Kush, Turtle Creek; Clayton J. Bossart, Monroeville, both of Pa.

[73] Assignee: Mine Safety Appliances Company, Pittsburgh, Pa.

[21] Appl. No.: 232,659

[22] Filed: Aug. 16, 1988

[51] Int. Cl.[4] .............................................. G01N 1/14
[52] U.S. Cl. .............................. 73/864.35; 73/864.62; 417/472; 417/63
[58] Field of Search .................. 417/472, 473, 63, 570, 417/571; 73/864.34, 864.35, 864.62

[56] References Cited

U.S. PATENT DOCUMENTS

| | | | |
|---|---|---|---|
| 2,648,331 | 8/1953 | Bennett | 417/472 |
| 3,119,272 | 1/1964 | Haunschild | 73/864.62 |
| 3,426,745 | 2/1969 | Farr | 73/864.62 |
| 3,612,722 | 10/1971 | Neward | 417/63 |
| 3,803,988 | 4/1974 | Orr | 417/571 |
| 3,981,632 | 9/1976 | LeFebre | 417/470 |
| 4,060,178 | 11/1977 | Miller | 417/473 |
| 4,594,051 | 6/1986 | Gaston | 417/63 |

FOREIGN PATENT DOCUMENTS

| | | | |
|---|---|---|---|
| 486396 | 11/1953 | Italy | 417/472 |
| 21881 | 11/1892 | United Kingdom | 417/473 |
| 4941 | 3/1915 | United Kingdom | 417/472 |

OTHER PUBLICATIONS

MSA Sales Bulletin Data Sheet 8-00-02, dated 1988.
Dragerwerk AG Lubeck Sales Information and Excerpts, dated Feb. 1983.
Sensidyne Sales Catalog, dated 1986.

*Primary Examiner*—Carlton R. Croyle
*Assistant Examiner*—Robert N. Blackmn
*Attorney, Agent, or Firm*—Douglas K. McClaine

[57] ABSTRACT

A hand-held air sampling pump can be operated with one hand to consistently sample an exact, predetermined volume of air by causing a bellows to compress and then elongate to form a vacuum inside of the bellows to draw an air sample through a detector tube and into the bellows.

3 Claims, 1 Drawing Sheet

BELLOWS TYPE HAND-OPERATED AIR SAMPLING PUMP

FIELD OF THE INVENTION

This invention relates to the field of hand-held and hand-operated air sampling pumps for atmospheric monitoring.

BACKGROUND OF THE INVENTION

In industrial applications, industrial hygienists are required to take periodic samples of the atmospheric breathing air in a given location. Hand-held, hand-operated air sampling pumps can be used to take such an air sample by drawing air through a chemical-reactive, colorimetric detection tube to determine the concentration of a certain chemical in the air sample.

There are several different types of manually-actuated hand-held sampling pumps that have been used to draw samples through detector tubes. These types may be, for example, a rubber or plastic squeeze bulb, a compressible bellows with spring return, or a manual or spring return piston pump.

The basic concept behind each of these pumps is to draw a specific volume of air sample through a colorimetric detection tube. The detector tubes are calibrated to react, by producing a stain length along a reactive agent inside of the tube as a specific volume of air, for example, 100 mL is drawn through the tube. The tubes can be calibrated to work with various volumetric sizes of samples. Once the volumetric flow is determined, however, it is essential that the precise amount of air be drawn through the tube during sampling. Accordingly, the accuracy of the concentration readings of the tube is directly proportional to the accuracy of the sample volume. For this reason, it is important that a sampling pump consistently draw an accurate amount of sampled air through the detector tube.

The three types of pumps are all similar in one aspect. In order to draw a sample of air, an air chamber inside of the pump is compressed or evacuated during a compression step. The evacuation of the air chamber causes a vacuum to form inside of the chamber. The vacuum then begins to dissipate by drawing air back into the air chamber through the detector tube.

Each type of pump provides a certain amount of accuracy and ease of operation. Ease of operation is an important feature of any sampling pump in that in many sampling situations, the pump must be able to be operated with one hand, for example, when a sample must be taken while climbing a ladder on a railroad car or a storage tank.

Of the three types of sampling pumps known, none can provide both accuracy, in drawing consistent volumes of air, and one-handed operation. The squeeze bulb type pump can be operated with one hand, however, it cannot draw consistent volumes of samples due to the inefficiency of evacuating its air chamber. An example of such a pump is the Thumbpump TM manufactured by Mine Safety Appliances Company, Pittsburgh, Pa. The piston pump is accurate in drawing sample amounts, however, the pump requires two hands to draw a sample. An example of a piston pump is the sampling pump manufactured by Sensidyne of Largo, Fla. The third pump, a spring-return bellows pump can provide both accuracy and one-hand operation. However, bellows pumps such as the Model 800-26065 manufactured by Dragerwerk AG Lubeck of the Federal Republic of Germany, cannot provide accurate results as the bellows cannot be completely and consistently evacuated during every compression step. The bellows of the Drager pump is comprised of two return springs and a rubber sleeve. Since the return springs of the bellows act alone as the stabilization frame of the pump, the bellows has a tendency to "cock" or deform during the compression step dependent upon how the user applies a force to compress the bellows. This results in a non-complete evacuation of the air chamber and an incomplete volumetric sample. Non-complete sampling can result in errors of 10-15% in determining the concentration of a chemical in the sample.

In all of these designs, a vacuum can still exist inside of the air chamber even though a visual inspection indicates that a complete sample has been drawn. In the piston type pumps, pressure indicators have been added to show when the vacuum has dissipated inside of the air chamber to indicate that a complete sample has been drawn. This feature is shown in the Sensidyne pump.

It would thus be desirable for a pump to provide the features of simple one-hand operation while drawing consistently accurate samples. It is the object of this invention to provide a hand-held air sampling pump that can be operated by one hand while consistently extracting precise volumes of sampled air from the atmosphere.

SUMMARY OF THE INVENTION

The present invention provides a hand-held sampling pump that can be operated with one hand. The pump incorporates a spring-operated bellows type air suction arrangement comprising a return spring, a rubber sleeve and a series of concentric stabilization rings. The bellows arrangement is supported inside of a lightweight rigid structure that acts to stabilize a plunger rod and the bellows during the compression stroke thereby causing the bellows to compress and elongate along a straight line. The stability caused by the frame ensures that the inner chamber of the bellows is uniformly evacuated during each compression stroke.

In use, a detector tube is inserted into the pump and the plunger rod is pushed in towards the bellows by the operator's hand. The plunger rod is attached to a compression plate that is mounted on one end of the bellows. The rod is held in place by the support frame so as to prevent lateral movement of the rod. During the compression stroke, the plunger compresses the bellows causing air to be expelled from the bellows as the air passes through a check valve that acts to open and close an expulsion port in the bellows. As the bellows spring begins to elongate after compression, a vacuum is created inside of the bellows. The vacuum causes air to be drawn through the detector tube through an intake port in the bellows. A check valve that acts to open and close the intake port is forced open as the air is drawn into the bellows. As the sample passes through the detector tube, a stain appears along a chemical bed inside of the tube, thereby indicating the concentration of a particular chemical in the air sample. Normally, in a bellows type arrangement, even though it visually appears that the bellows is fully extended, the vacuum inside of the bellows sleeve continues to cause air to be drawn into the sleeve for several more seconds. To assure the operator that the proper amount of air has been drawn through the tube and that a complete sample has been taken, a pressure indicator is used to show when the pressure inside of the sleeve has returned to atmospheric indicating the end of the sample draw.

DESCRIPTION OF THE PREFERRED EMBODIMENT

Figure 1:
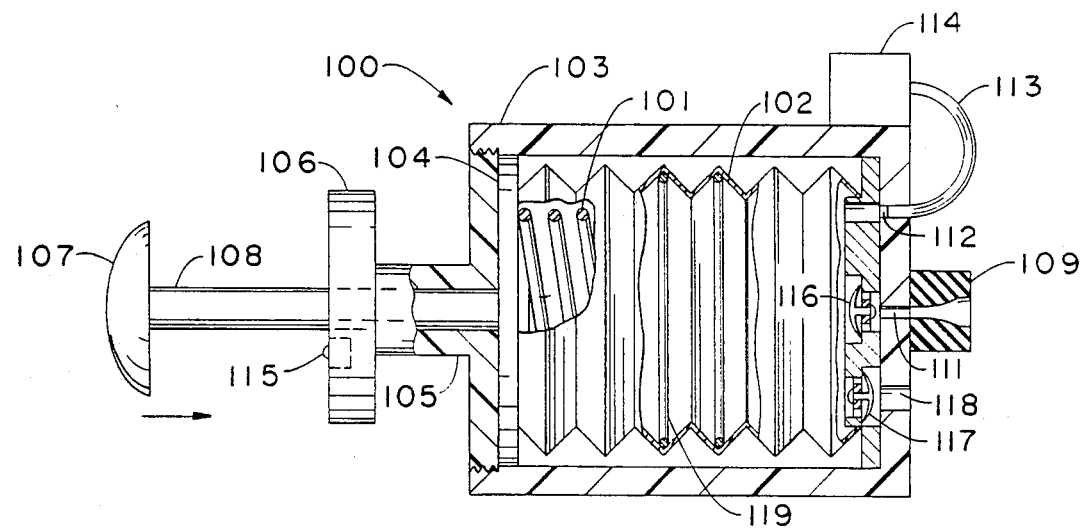
FIG. 1 is a schematic view of a hand-held, bellows-type sampling pump showing the pump with the bellows extended in a relaxed state.

Referring first to FIG. 1, a hand-held sampling pump 100 is shown. The pump 100 uses a bellows assembly to draw an air sample into the pump. The bellows assembly has a spring 101 and approximately six concentric stabilization rings 119 that are enclosed by an airtight flexible sleeve 102. The sleeve 102, which may be made of a rubber material for example, forms a virtually airtight inner chamber around the spring 101 and rings 119. The bellows arrangement is positioned inside of a rigid frame 103 that surrounds the outer perimeter of the bellows. The frame 103 maintains and stabilizes the position of the bellows, so that after the spring 101 is compressed, the spring elongates to its normal position along a straight line. This prevents the spring 101 from deforming or "cocking" during compression or elongation to prevent volumetric variations in the volume of the air sample. One end of a hollow tube or throat 105 is attached to the frame 103. The other end of the tube 105 is inserted through a hole cut through a handgrip stop 106. The stop 106 is then rigidly affixed to the hollow tube 105.

A rod or plunger 108 is inserted into the hollow tube 105 so that the plunger can be slid along the inside of the tube 105. The hollow tube 105 prevents the plunger rod 108 from moving laterally during use. A hand pad 107 is attached at one end of the plunger 108 to enable the user to press against the plunger 108 without injuring the user's palm. The opposite end of the plunger 108 is rigidly attached to the center of a flat circular compression plate 104 that is secured to one end of the bellows spring 101 and sealed around its outer circumference by the bellows sleeve 102.

At the opposite end of the bellows, an expulsion port 118 is formed in the mounting frame 103. The expulsion port 118 is covered by a check valve 117 that permits air from the inner chamber of the bellows to be expelled from the bellows while preventing air from flowing back into the bellows. A detector tube mounting assembly 109, made of rubber for example, is attached to the mounting frame 103 around an intake port 111. The tube mounting assembly 109 acts to receive and hold a detector tube (not shown) during sampling. The intake port 111 is covered by a check valve 116 that acts to permit air flow into the bellows and then to prevent air flow out of the bellows and detector tube during the compression stroke.

A third port 112 is formed in the mounting frame 103 to receive a pressure indicator hose 113. At one end of the hose, a pressure indicator 114 is mounted on the pump frame 103 and attached to the opposite end of the indicator hose 113. The pressure indicator 114 indicates when the pressure inside of the bellows sleeve 102 has returned to atmospheric thereby indicating that the internal vacuum of the bellows has dissipated and that the pump has drawn the correct volume of sampled air through a detector tube.

Figure 2:
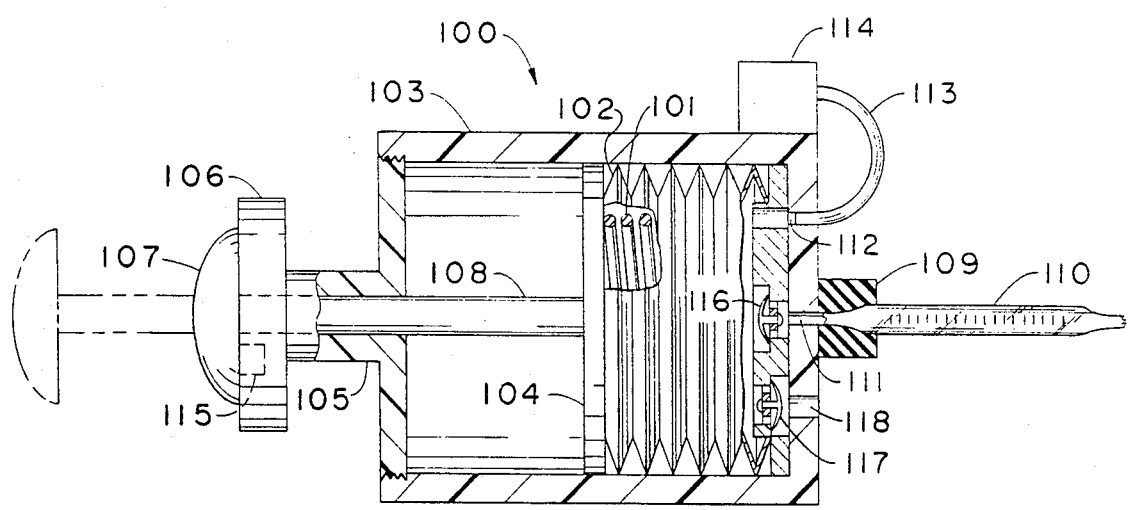
FIG. 2 is a schematic view of a hand-held, bellows-type sampling pump showing the pump during a compression stroke with the bellows compressed in an evacuated state.

Referring now to FIG. 2, the sampling pump 100 is shown during the compression stroke of the pump. In operation, the user breaks off both ends of a detector tube 110 and inserts one end into the detector tube mounting assembly 109. The user then grasps the handle of the pump 106 as if grasping a pistol grip as the hand pad 107 is positioned in the palm of the user's hand. By squeezing the hand, a pressure is exerted by the palm against the hand pad 107 causing the plunger 108 to push against the center of the bellows compression plate 104. As the bellows plate 104 moves against the bellows spring 101, the spring 101 is compressed against the pump frame 103 until the hand pad 107 is stopped by contacting the handgrip stop 106. As the spring 101 is compressed, the air inside of the bellows sleeve 102 is expelled around the check valve 117 and through the bellows expulsion port 118. At this stage, the pressure indicator 114 registers a zero pressure inside of the bellows sleeve 102 as the air inside of the bellows is evacuated.

When the user relaxes his hand, the bellows spring 101 begins to elongate forcing the bellows sleeve 102 and stabilization rings 119 apart until the spring 101 returns to its natural length. As the spring elongates, a vacuum is created inside of the bellows sleeve 102 and a negative pressure is indicated by the pressure gauge 114. The vacuum inside of the sleeve 102 causes air to be drawn into the bellows sleeve 102 through the open ends of the detector tube 110 around the intake check valve 116 through the intake port 111. As the spring 101 returns to its normal position, the plunger 108 and hand pad 107 are forced back out of the pump frame 103. Air continues to be drawn through the intake port 111 and detector tube 110 until the vacuum dissipates inside of the bellows sleeve 102.

The length of compression of the bellows sleeve 102 and spring 101 determines the volumetric size of the air sample that is drawn into the pump. For example, to draw a 100 mL sample of air into the pump, a spring that is 1.74 inches outer diameter and 3.25 inches long is compressed 1⅜ inches by the plunger 108. The length of the plunger 108 between the hand pad 107 and the handgrip stop 106 determines the length of compression of the spring 101 and sleeve 102 and hence, the size of the sample that is drawn. To vary the size of sample, the length of the distance between the hand pad 107 and handgrip stop 106 can be increased or decreased. A mechanical stroke counter 115 can also be positioned on the handgrip 106 to indicate the number of times that the hand pad 107 has been compressed against the handgrip 106 thereby indicating the number of compression strokes that have been taken. In order to take a 200 cc sample, the user may compress the spring a second time after the first compression stroke is completed. By compressing the spring linearly inside of a rigid frame, the user can be certain that the proper length of spring compression is achieved. This is unique over prior art pumps, such as the Drager Device, where the two bellows springs and sleeve can be distorted or cocked during compression thereby requiring the user to squeeze the pump with both hands to attempt to completely compress the spring. In the present invention, by positioning the plunger rod 108 inside of the rigid throat 108; by fixedly attaching the rod 108 to the center of the compression plate 104 of the bellows and by positioning concentric stabilization rings 119 inside of the bellows, the bellows is compressed linearly and does not distort or move laterally during the compression stroke or while the bellows is drawing air. As a result, accurate volumetric samples can be taken repeatedly and consistently.

The principles of the invention have been illustrated and described in what is now considered to be its best embodiment. However, it is to be understood that within the scope of the appended claims, the invention may be practiced otherwise than as specifically illustrated and described.

What is claimed is:

1. A sampling pump comprising:
   a. a bellows having a flexible airtight sleeve that encompasses a return spring and a plurality of rigid concentric stabilization rings and having a first and second opening at a first end;
   b. a rigid frame positioned around the outer perimeter of said bellows, having a hollow sleeve at one end adapted to receive and position a plunger rod while permitting movement of said rod therethrough, a handgrip means extending outwardly from said sleeve to enable the pump to be held and said plunger rod to be moved with one hand;
   c. a compression plate attached to a second end of said bellows that is rigidly attached to said plunger rod at the center of said plate;
   d. a retaining means suitable for receiving and retaining a colorimetric detector tube positioned at said first bellows opening;
   e. a check valve positioned to permit air flow into said bellows through said first opening of said bellows while preventing air flow out of said bellows; and,
   f. a second check valve positioned to permit air flow out of said second opening of said bellows while preventing air flow into said bellows.

2. A sampling pump according to claim 1 where a pressure indicating means is fluidically attached to said bellows to indicate the presence or absence of a negative pressure inside of said bellows.

3. A sampling pump according to claim 1 where a means is attached to said frame to indicate the number of compression strokes taken during a sampling period, by indicating the number of times that said plunger contacts the frame of the sampling pump.

* * * * *